United States Patent [19]

D'Hinterland et al.

[11] 3,998,947

[45] Dec. 21, 1976

[54] PROCESS FOR OBTAINING A PLASMINOGEN ACTIVATOR

[75] Inventors: Lucien Dussourd D'Hinterland, Castres; Lucien Pradayrol, Toulouse; Jacques Durand; Gerard Normier, both of Castres, all of France

[73] Assignee: Pierre Fabre, S.A., Paris, France

[22] Filed: Dec. 3, 1974

[21] Appl. No.: 529,147

[30] Foreign Application Priority Data

Dec. 3, 1973  France ............................. 73.42891

[52] U.S. Cl. .............................. 424/105; 424/98; 424/103; 424/101; 424/94; 260/112 R
[51] Int. Cl.² ...................................... A61K 35/48
[58] Field of Search .................... 424/105, 101, 98; 260/112 R

[56] References Cited

UNITED STATES PATENTS

| | | | |
|---|---|---|---|
| 3,234,106 | 2/1966 | Hink et al. | 424/101 |
| 3,743,722 | 7/1973 | Nolan | 424/98 |

OTHER PUBLICATIONS

Kok et al., Biochemistry, vol. 8, No. 1, pp. 79–86 (1969).
Bachmann et al., Biochemistry, vol. 3, p. 1578 (1964).
White et al., Biochemistry, vol. 5, No. 7, pp. 2160–2169 (1966).
Keio Journal of Medicine, vol. 13, No. 4, Dec. 1964 pp. 187–194.
Brockway et al., J. of Biological Chemistry, vol. 246, No. 14 Issue of July 25, 1971, pp. 4641–4647.
Science, vol. 170, No. 3959, Nov. 13, 1970, pp. 1095 & 1096.

*Primary Examiner*—Donald B. Moyer
*Attorney, Agent, or Firm*—Alan H. Levine

[57] ABSTRACT

A process for obtaining a plasminogen activator involves treating an acetone extract powder of organs of animals, such as the lungs and kidneys of pigs, calves, bullocks, horses, lambs or sheep or the ovaries of porcine, bovine or ovine animals, by suspension in an aqueous saline solution, taking up the precipitate obtained in an aqueous saline solution of greater ionic strength and lower pH-value, decanting the solution and precipitating therefrom at acidic pH by adding a salt or an organic solvent, further taking up the precipitate obtained in water or a saline solution, followed by repeated precipitation by adding a salt at a somewhat higher pH-value, finally taking up the precipitate obtained in water and dialyzing the solution, and optionally purifying the solution obtained.

The activator obtained may be used as a medicament.

15 Claims, No Drawings

PROCESS FOR OBTAINING A PLASMINOGEN ACTIVATOR

BACKGROUND OF THE INVENTION

An activator of the type with which the invention is concerned is already known, namely urokinase, which is extracted from the urine of mammals (cf. U.S. Pat. Nos. 2,961,382; 2,983,647 and 2,989,440). However, it has been found that urokinase is very sensitive to induced inhibitors and that its effect diminishes very quickly.

Accordingly, there is a need for an activator which is at least equivalent to urokinase in regard to activity, but which is unaffected by inhibitors.

OBJECTS OF THE INVENTION

Accordingly, the object of the invention is to provide a process for extracting and purifying a tissular, endocellular plasminogen activator extracted from the organs of animals. The activator extracted and purified in accordance with the invention acts on the peptidic arginine-valine bonds in plasminogen by opening these bonds without breaking the disulphide bridges, thus converting the plasminogen into plasmin in accordance with the following global scheme:

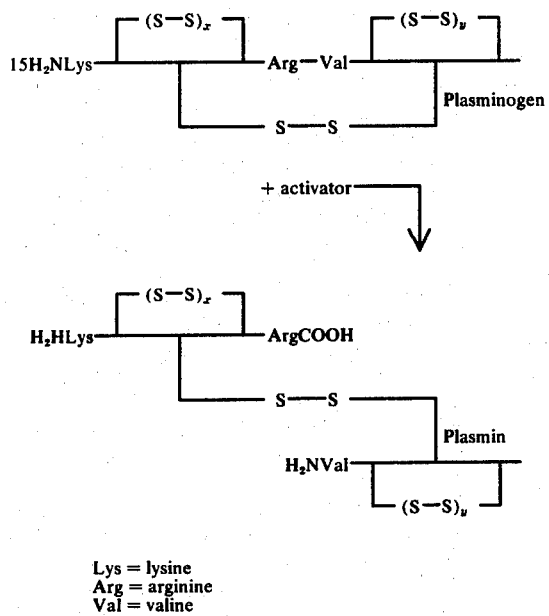

Lys = lysine
Arg = arginine
Val = valine

Lys = lysine
Arg = arginine
Val = valine

The plasmin or fibrinolysine thus formed, which increase the lysis rate of the fibrin clots, makes the product according to the invention particularly valuable as a medicament for the treatment of, in particular, arterial and venous thrombosis.

SUMMARY OF THE INVENTION

According to the invention, the object as stated above is achieved by a process for obtaining a plasminogen activator, in which an acetone extract powder of animal organs, such as the lungs and kidneys of pigs, calves, bullocks, horses, lambs or sheep, or the ovaries or porcine, bovine or ovine animals, is treated by:

a. suspending said powder in an aqueous saline solution having a low ionic strength and a pH around the neutral point;

b. taking up the precipitate obtained in stage (a) in an aqueous saline solution with an ionic strength of about 0.6 to 1 at a pH-value in the range from about 3 to 5;

c. precipitating from the solution obtained in stage (b) and after decantation, by adding a salt or an organic solvent at a pH-value in the range of from about 3 to 5;

d. taking up the precipitate obtained in stage (c) in water or a saline solution, followed by precipitation by adding a salt at a pH-value of or slightly above, 7;

e. taking up the precipitate obtained in stage (d) in water and dialysing the solution up to a resistivity level of the order of 1000 ohm.cm at 10° C, and f. optionally purifying the solution obtained.

The salt used in stage (a) is preferably potassium acetate or potassium chloride used in a concentration of from about 1 to 10 g per liter.

The salt used in stage (b) is preferably a potassium salt, more especially potassium chloride, potassium acetate or potassium sulphate, used in a concentration of from about 20 to 80 g per liter, the pH-value being adjusted to between 3 and 5, preferably by adding an acid such as acetic acid or sulphuric acid in such a way that the ionic strength of the solution is between 0.6 and 1.

The salt used in stage (c) is preferably ammonium sulphate or sodium chloride used in a concentration of from 100 to 200 g per liter.

Although it is possible in stage (c) to precipitate the solution by adding an organic solvent, such as acetone, it is preferred to use salting out with a salt which increases the yield of the operation.

The salt used in stage (d) is preferably sodium chloride, ammonium sulphate or potassium sulphate, the pH-value being adjusted to a value slightly higher than 7 by adding a base such as soda.

Stages $a$ and $b$ of the process are preferably carried out at a temperature of the order of 4° C.

The organs treated in the process according to the invention are removed from animals immediately after death and then mechanically fat-extracted and ground up.

The organs thus coarsely ground are frozen and, if necessary, may be reground in frozen form and then unfrozen in suspension in a buffer with a low ionic strength and a pH-value of from 5 to 7 in order to be homogenised.

In one preferred embodiment of the invention, the acetone powder of animal organs is obtained by dispersing the ground, homogenised organs in an acetone bath at low temperature, for example at a temperature of the order of −10° C. The acetone powder is obtained by filtration and drying the preceding suspension.

The purification stages preferably comprise a precipitation stage at the isoelectric pH-value. To this end, the solution obtained in stage $e$, which has a resistivity of 1000 ohm.cm, is adjusted to a pH-value of around 6.8, after which the ionic strength of the solution is adjusted to $10^{-2}$ by adding a salt, such as calcium chloride, but preferably a zinc salt, such as zinc acetate or zinc chloride, after which the solution is left at 0° C in order to complete precipitation. The precipitate thus obtained may be preserved after dialysis by lyophilisation.

If desired, complete purification may be obtained by exclusion chromatography on a mixed gel of dextranagarose and polyacrylamide, such as a Sepharose 6 B gel, in order to eliminate certain molecular impurities, and/or by chromatography on an ion exchanger in order to eliminate the ionic impurities. Resins which may be used for this purpose are, for example, weakly acid or mixed exchangers such as the resins Bio rex 70, in which case elution is carried out at a constant ionic strength and at an increasing pH-value, AG 11 $A_8$ Biorad, in which case elution is carried out at a constant pH-value and with an increasing ionic strength, or Biogel H.T.P., in which case elution is carried out by varying the ionic strength.

The ionic stengths of the solutions are calculated from the resistivity of the solutions as measured by known methods.

A general scheme of the preparation of enzymatically active molecules in accordance with the present invention is given hereinafter in order to illustrate the preferred embodiment of the invention.

I - PREPARATION OF THE ACETONE POWDER

The above-mentioned organs are removed from the animals immediately after death and then mechanically fat-extracted and ground up.

After grinding, the organs are quickly frozen. They will subsequently undergo grinding in frozen form and will be homogenised after having been unfrozen in a phosphate buffer with a low ionic strength and a pH-value in the range from 5 to 7.

The organs thus prepared are dispersed in an acetone bath of which the temperature should be no higher than $-10°$ C.

After an adequate contact time, the suspension is filtered under a moderate vacuum.

The filter cake is carefully dried by passing nitrogen through it at low temperature.

The acetone powder thus obtained is pink in colour and is subjected to fine homogenisation after drying.

II - OBTAINING AN ENRICHED EXTRACT a. Prewashing the acetone powder:

This operation is intended to eliminate from the outset a number of weakly bonded pigments and proteins which could otherwise interfere with extraction.

The acetone powder is suspended in an aqueous solution of a salt whose ionic strength will remain low, the pH-value of the solution remaining between 5 and 8, preferably around the neutral point. After stirring for 1 hour at 4° C, the residue of acetone powder is decanted, the solution clarified, for example in a centrifuge with a decanting bowl, and the residue thus obtained added to the above residue.

b. Extraction:

In this operation, the residue from stage (a) is taken up in a medium with a higher ionic strength and a pH-value of from 3 to 5, the ionic strength of the solution being fixed between 0.6 and 1 by the addition of a potassium salt.

This extraction medium is stirred for at least 2 hours at a temperature maintained at 4° C.

The ratio by weight of acetone powder to solvent should not exceed 5 %.

The unextracted acetone powder residue is eliminated by centrifuging and the solution recovered is filtered under nitrogen pressure on an EKS filter.

c. Precipitation in acid medium:

This initial precipitation of the solution obtained beforehand is carried out in acid medium at a pH-value of around 4.5 by adding a semi-saturated salting-out agent, such as ammonium sulphate, at 10° C. The precipitate thus obtained is taken up in a volume of water or saline solution with a resistivity below 800 ohm.cm at 10° C, the volume of that solution preferably not exceeding one quarter of the volume of the extracted solution.

d. Precipitation in weakly basic medium:

The pH-value of the solution obtained beforehand is increased to a value slightly higher than 7 by the addition of soda (pH-value between 7 and 8). The solution thus obtained is precipitated by the addition of a large quantity of a salt, for example ammonium sulphate in a quantity of 200 g per liter, potassium sulphate in a quantity of 200 g per liter or sodium chloride in a quantity of 185 g per liter.

The precipitate is taken up with water, the volume of the solution thus formed being approximately 1/10th of the volume of the extract treated in stage (b).

e. Dialysis:

The solution thus obtained is dialysed up to a resistivity level of the order of 1000 ohm.cm at 10° C. The product at this level may follow the subsequent phases of purification or may even be preserved by lyophilisation.

III - PURIFICATION OF THE ENRICHED EXTRACT

1. Purification by precipitation at a pH-value around the isoelectric pH

The dialysate obtained in stage (e) is adjusted to the isoelectric pH of the enzyme, i.e. pH 6.8, followed by the careful addition of a saline solution, preferably of zinc acetate, to adjust the ionic strength to $10^{-2}$. This is followed by stirring overnight at 0° C to obtain precipitation.

The precipitate is recovered and redissolved in 1/20th of the volume of the initial extract.

2. Exclusion chromatography

The product obtained in the preceding stage or in stage (e) is passed through a column of Sepharose 6 B balanced with a phosphate buffer whose ionic strength is adjusted to 0.6 by the addition of sodium or potassium chloride.

The ratio between the height of the gel to the diameter of the column should not be any less than 10. The chromatography rate is fixed between 0.8 and 1 liter per hour for a column with a volume of 10 liters, the volume of the sample applied being from 500 to 800 ml for a column such as previously envisaged (which corresponds to approximately 10 kg of untreated organs).

Chromatography is carried out at a temperature of 4° C followed by recovery of the eluted fraction which amounts to between 15 and 25 liters for a 10 liter column.

The product obtained may be concentrated by cold precipitation with alcohol or acetone (3 volumes), or may even by lyophilised after dialysis.

3. Purification on an ion exchanger

On a weakly acid cation-exchanger resin:

The resin used is a Bio rex 70 resin balanced in an acetate buffer balanced to 4.5. Elution is carried out with solutions having a constant ionic strength but an increasing pH-value. The product is collected from the eluted fraction at pH 5.2 to 5.7.

On mixed resin:

The resin used is a mixed resin AG 11 A$_8$ balanced to a resistivity of greater than 8000 ohm.cm. A solution of the enriched extract is treated in a weakly acid medium.

Elution is carried out at an increasing ionic strength and the product is recovered from the eluted fraction at a resistivity of around 5000 ohm.cm.

On Biogel H.T.P.

The apatic hydroxyl is balanced in an M/100 phosphate buffer at pH 6.8. The suspension of Biogel H.T.P. in this buffer is stirred for 30 minutes with 10 ml of crude extract per gram of dry absorbent. Following elimination of the solution by filtration or centrifuging, the sediment is recovered and the resistivity of the supernatant phase adjusted to a value below 80 ohm.cm. After re-centrifuging, the dialysed supernatant phase is lyophilised.

4. Purification by affinity chromatography

Affinity chromatography is carried out on a support of the type: AH - Sepharose 4 B, to which a specific inhibitor of the plasminogen activator has been fixed by a carbodiimide.

The inhibitors which may be used for this purpose are, for example, ϵ-amino caproic acid, aminoethyl cyclohexanoic acid, trans-4-aminoethyl cyclohexane carboxylic acid, paraaminomethyl benzoic acid.

Affinity chromatography may also be carried out on a CN Br-activated Sepharose to which lysine or any of the above-mentioned products may be fixed.

Any other support suitable for fixing may also be successfully used, such as for example the Biogel series.

The plasminogen activator is dissolved in a 0.1 M phosphate buffer of pH 7 – 7.2, and the resulting solution passed through a column containing one of these supports. The activity remains fixed to the support, whilst the inactive proteins are eluted. The acitivity is then eluted by means of an ionic strength gradient, and the active fraction may be treated by the following two methods:

1. precipitation by means of a salt, such as ammonium sulphate, dialysis followed by lyophilisation;
2. precipitation in the form of an insoluble complex at an acid pH with a polysaccharide, dissolution of the complex at a neutral pH-value and lyophilisation.

The invention is illustrated by, but by no means limited to, the following Examples.

The acetone powder used in these Examples is obtained from the ovaries of sows by method I described above.

DESCRIPTION OF SPECIFIC EMBODIMENTS

EXAMPLE 1 a. 1 kg of the acetone powder obtained in the manner described above is suspended in 50 ml of a 10 g/l potassium acetate solution. After stirring for 1 hour, the suspension is decanted. The clear supernatant phase is removed.

b. 50 liters of cold water, 1.5 kg of potassium acetate and 1 liter of glacial acetic acid are added in that order to the precipitate obtained, followed by vigorous stirring for at least 3 hours. The insoluble fraction is eliminated by centrifuging, and the solution filtered.

c. 7.5 kg of ammonium sulphate are then added tohis this solution followed by stirring to obtain com-lis-plete dissolution. After standing for at least 3 su-hours, the supernatant solution is removed andate the precipitate redissolved in 10 liters of a 10ι g/l potassium acetate solution.

d. The pH-value of this solution is adjusted to pH 10 with soda, followed by the addition of 2 kg of ammonium sulphate. After standing for 2 hours to obtain precipitation, the precipitate is collected and dissolved in 5 liters of water.

e. The solution is dialysed overnight against running water.

f. The insoluble fraction formed during dialysis is removed, and the solution subsequently treated with 500 mg of calcium chloride, the pH adjusted to 6.5 and the solution dialysed again against 30 liters of a 100 mg/l calcium chloride solution. After dialysis for 4 hours, the precipitate formed is redissolved in 1 liter of water with 5 cc of acetic acid. The solution is lyophilised.

EXAMPLE 2 a. 1 kg of acetone powder obtained in the manner described above is suspended in 50 liters of cold water. 50 g of potassium chloride are added to the resulting solution, followed by stirring. After decantation, the solution is eliminated through a floating filter.

b. The solid phase is resuspended in 50 l of water to which 1.750 kg of potassium chloride and 500 ml of glacial acetic acid are added in that order. Homogenisation is followed by stirring for 6 hours, after which the solution is filtered.

c. The solution is then treated with 5 kg of sodium chloride, the precipitate obtained being redissolved in 10 liters of a 20 g/l sodium chloride solution.

d. After the solution has been neutralised by the addition of soda, 1.750 kg of sodium chloride are added. The insoluble fraction thus obtained is taken up in 5 liters of water and dialysed overnight against running water.

e. The insoluble fraction left after dialysis is eliminated and the supernatant solution precipitated by the addition of 3 volumes of acetone at −20° C. The precipitate redissolved in a minimum quantity of water is applied to the top of a column of Sepharose 6 B (10 × 200) balanced in a phosphate buffer at pH 7.2. The product is recovered in the eluted fraction amounting to between 2 and 2.5 times the volume of the column. The solution thus obtained is dialysed and lyophilised.

EXAMPLE 3 a. 1 kg of acetone powder obtained in the manner described above is suspended in 50 liters of cold water to which 200 g of potassium acetate are added. The pH-value of the solution is adjusted to pH 8 by the addition of soda. Stirring for 15 minutes is followed by decantation, after which the supernatant solution is removed.

b. The solid residue obtained above is suspended in 50 liters of water to which 3 kg of potassium sulphate and sulphuric acid are added, the sulphuric acid in a quantity sufficient to adjust a pH of or below 5. Homogenisation is followed by stirring for 3 hours in the absence of heat. The insoluble fraction is eliminated and the soluble fraction filtered on an EKS filter.

c. The filtrate is treated with 2 volumes of acetone at −20° C. The precipitate obtained after decantation is redissolved in 10 liters of water.

d. 2 kg of potassium sulphate are added to the resulting solution. After the solution has been neutralised, a precipitate is recovered by centrifuging and is redissolved in 5 liters of water.

e. The solution thus obtained is passed through an ion-exchange column of AG 11 $A_8$ balanced in a slightly acid medium (500 g of dry exchanger per liter of sample). Elution is carried out at an increasing ionic strength and at a slightly acid pH-value. The active product is recovered in the eluted fraction having a resistivity of 5000 ohm.cm.

STUDY OF PHARMACOLOGICAL PROPERTIES

The product studied is the product obtained after precipitation of the solution at the isoelectric point.

1. Character of the molecule

The molecule is a glycoprotein-type molecule with a molecular weight of approximately 40,000. Monomers and polymers common to all the enzymatic substances are formed. The molecule has an isoelectric point (or isoelectric pH) of 6.8.

The molecule is soluble in a phosphate buffer having an ionic strength of 2000 ohm.cm.

2. Pharmacological properties

The product obtained contains from 300 to 500 CTA units per milligram. The active site is fixed on the peptidic arginine-valine bonds of the plasminogen which are opened without breaking the disulphide bridges, thus converting the plasminogen into plasmin.

The molecule thus acquires a high level of mobility by rotation about the disulphide bridges, thus enabling it to develop its enzymatic activity and to become localised around the receptors.

In vitro tests carried out on plates of fibrin by Astrup's method show that the product of the lysis diameters for a 40 ug/cc solution is greater than 400 mm².

It is not possible to detect any lysis zones on a plate heated for 30 minutes at 80° C (destruction of the plasminogen).

Nor is there any evidence of esterasic activity with respect to the following amino acid esters: L-lysine, L-phenyl alanine, L-tryptophane, etc. It is only the methyl ester of paratosyl arginine and paranitrophenyl-N-carbobenzoxy-L-tyrosine that are lysed.

The in vivo tests carried out by von Kaula's method, by measuring the lysis time of the plasmatic euglobulins in rats by the intravenous injection of a 25 mg/kg isotonic solution of the product described above, produces a reduction of 50 % in the lysis time of the euglobulin clot, which is reflected in significant activation of the circulating fibrinolytic system.

Accordingly, the product according to the invention is particularly valuable as a medicament in the treatment of arterial and venous thrombosis and in the treatment of fibrinous deposits. The product is preferably administered by slow intravenous injection or by perfusion.

What is claimed is:

1. A process for obtaining a plasminogen activator, wherein an acetone extract powder of the ovaries of sow obtained by grinding of the ovaries, dispersing the ground ovaries in acetone at a temperature below −10° C, filtering the suspension, drying the filter cake obtained, is treated by:
   a. suspending said powder in an aqueous saline solution having an ionic strength between 0.1 and 0.01 and a pH in the range from 5 to 8;
   b. taking up the precipitate obtained in stage (a) in an aqueous saline solution with an ionic strength of 0.6 to 1 at a pH-value in the range of from 3 to 5;
   c. precipitating the solution obtained in stage (b) after decantation, by adding a salt or acetone at a pH-value in the range from 3 to 5;
   d. taking up the precipitate obtained in stage (c) in water or a saline solution, followed by precipitation by adding a salt at a pH-value of or slightly above 7;
   e. optionally purifying the plasminogen activator of the precipitate obtained.

2. A process as claimed in claim 1, wherein the salt used in stage (a) is selected from the group consisting of potassium acetate and potassium chloride, employed in concentrations of from about 1 to 10 g/l.

3. A process as claimed in claim 1, wherein the salt used in stage (b) is a potassium salt.

4. A process as claimed in claim 3, wherein the salt is selected from the group consisting of potassium chloride, potassium acetate or potassium sulphate.

5. A process as claimed in claim 1, wherein the salt used in stage (c) is selected from the group consisting of ammonium sulphate and potassium chloride, employed in concentrations of from 100 to 200 g/l.

6. A process as claimed in claim 1, wherein the salt used in stage (d) is selected from the group consisting of sodium chloride, ammonium sulphate and potassium sulphate.

7. A process as claimed in claim 1, wherein stages (a) and (b) of the process are carried out at temperatures of the order of 4° C.

8. A process as claimed in claim 1, wherein stage (e) is carried out by dissolving the precipitate obtained in stage (d) and precipitating the solution obtained at the isoelectric pH of 6.8 by means of a salt selected from the group consisting of zinc acetate, zinc chloride and calcium chloride.

9. A process as claimed in claim 1, wherein the precipitate is purified by:
   dissolving the precipitate in water,
   dialysing the solution against running water,
   removing the insoluble fraction formed during dialysis,
   treating the solution with calcium chloride to a concentration of 100 mg/l,
   dialysing the solution obtained against a 100 mg/l calcium chloride solution,
   taking up the precipitate in water and lyophilising the solution.

10. A process as claimed in claim 1, wherein the precipitate is purified by:
    dissolving the precipitate in water,
    dialysing the solution against running water,
    removing the insoluble fraction formed during dialysis,
    precipitating the solution by acetone at −20° C,
    dissolving the precipitate in water,
    passing the solution through column of resin Sepharose 6 B balanced in a phosphate buffer at pH 7.2,
    recovering the eluted fraction amounting to between 1.5 and 2.5 times the volume of the column.

11. A process as claimed in claim 1, wherein the precipitate is purified by:
    dissolving the precipitate in water,
    passing the solution through an ion exchange column of AG 11 $A_8$ balanced in acid medium and to a resistance of greater than 8000 $\Omega$.cm, eluting at an increasing ionic strength and at acid pH-value,
recovering the eluted fraction having a resistivity of 5000 Ω.cm.

12. A process as claimed in claim 1, wherein the precipitate is purified by:
dissolving the precipitate in water,
dialysing the solution against running water,
removing the insoluble fraction formed during dialysis,
contacting the solution with Biogel HTP balanced in a M/100 phosphate buffer at pH 6.8,
eliminating the solution and dissolving the sediment,
adjusting the resistivity of the supernatant phase to a value below 80 Ω.cm,
recovering the supernatant phase which contains the plasminogen activator.

13. A process as claimed in claim 1, wherein the precipitate is purified by:
dissolving the precipitate in water,
dialysing the solution against running water,
removing the insoluble fraction formed during dialysis,
passing the solution on a resin Biorex 70 balanced in an acetate buffer balanced to pH 4.5,
eluting with solution having a constant ionic strength but an increasing pH-value,
collecting the eluted fraction at pH 5.2 to 5.7.

14. A process as claimed in claim 1, wherein the precipitate is purified by an affinity chromatography by dissolving the plasminogen activator in a 0.k M phosphate buffer of pH 7 to 7.2, passing the solution on a support AH Sepharose 4 B to which a specific inhibitor of the plasminogen activator selected from the group consisting of ε-amino caproic acid, aminoethyl cyclohexanoic acid, trans 4-aminomethyl cyclohexane carboxylic acid, paraaminomethyly benzoic acid, eluting the active fraction with an ionic strength gradient.

15. A process for treatment of arterial and venous thrombosis which comprise administration of the plasminogen activator obtained according to claim 1.

* * * * *